(12) United States Patent
Yoon et al.

(10) Patent No.: US 7,795,463 B2
(45) Date of Patent: Sep. 14, 2010

(54) PROCESS FOR PREPARING DIISOPROPYL ((1-(HYDROXYMETHYL)-CYCLOPROPYL) OXY)METHYLPHOSPHONATE

(75) Inventors: Suk-Kyoon Yoon, Daejeon (KR); Kun-Hye Nam, Daejeon (KR); Sang-Who Lee, Daejeon (KR); Won-Kyo Joung, Daejeon (KR); Sang-Chul Choi, Daejeon (KR); Ki-Kon Lee, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 688 days.

(21) Appl. No.: 11/631,263

(22) PCT Filed: Jun. 27, 2005

(86) PCT No.: PCT/KR2005/002007

§ 371 (c)(1),
(2), (4) Date: Mar. 27, 2007

(87) PCT Pub. No.: WO2006/004330

PCT Pub. Date: Jan. 12, 2006

(65) Prior Publication Data

US 2009/0187019 A1    Jul. 23, 2009

(30) Foreign Application Priority Data

Jul. 2, 2004  (KR) .................. 10-2004-0051558

(51) Int. Cl.
C07F 9/40 (2006.01)
C07C 43/164 (2006.01)
(52) U.S. Cl. .................. 558/141; 558/188; 558/189; 568/660
(58) Field of Classification Search ................ 558/141, 558/188, 189
See application file for complete search history.

(56) References Cited

U.S. PATENT DOCUMENTS

| 5,688,778 | A | 11/1997 | Kim et al. | |
|---|---|---|---|---|
| 5,817,647 | A | 10/1998 | Casara et al. | |
| 7,157,448 | B2 * | 1/2007 | Choi et al. | 514/81 |
| 2006/0052346 | A1 * | 3/2006 | Averett | 514/81 |
| 2006/0111324 | A1 * | 5/2006 | Choi et al. | 514/81 |

FOREIGN PATENT DOCUMENTS

| WO | WO-93/07157 A1 | 4/1993 |
|---|---|---|
| WO | WO-02/057288 A1 | 7/2002 |

OTHER PUBLICATIONS

Greene et. al. (Greene's Protective Groups in Organic Synthesis, 4th Edition, 2006, pp. 153-156).*

J. Choi et al., "A Novel Class of Phosphonate Nucleosides, 9-[(1-Phosphonomethoxycyclopropyl)methyl]guanine as a Potent and Selective Anti-HBV Agent", J. Med. Chem., vol. 47, 2004, pp. 2864-2869.

* cited by examiner

Primary Examiner—James O Wilson
Assistant Examiner—Susanna Moore
(74) Attorney, Agent, or Firm—Birch, Stewart, Kolasch & Birch, LLP

(57) ABSTRACT

Disclosed is a process for preparing a compound of the following formula (2):

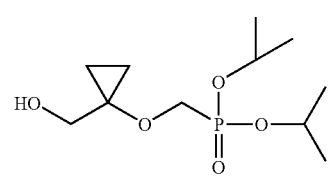

(2)

including the steps of reacting a compound of the following formula (4):

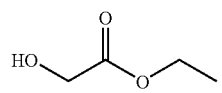

(4)

with trityl chloride to prepare trityloxy-acetic acid ethyl ester of the following formula (8):

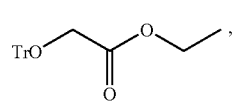

(8)

reacting the compound of formula (8) with ethyl magnesium halide to prepare 1-trityloxymethyl-cyclopropanol of the following formula (9):

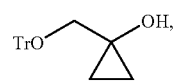

(9)

combining the 1-trityloxymethyl-cyclopropanol of formula (9) with diisopropylbromo-methylphosphonate in a solvent in the presence of a base to prepare (1-trityloxymethyl-cyclopropoxymethyl)-phosphonic acid diisopropyl ester of the following formula (10):

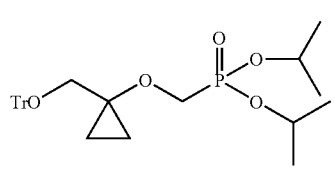

(10)

as a solid form, and converting the trityl group of the compound of formula (10) into a hydroxyl group.

8 Claims, No Drawings

PROCESS FOR PREPARING DIISOPROPYL ((1-(HYDROXYMETHYL)-CYCLOPROPYL) OXY)METHYLPHOSPHONATE

TECHNICAL FIELD

The present invention relates to a new process for preparing a compound of the following formula (2):

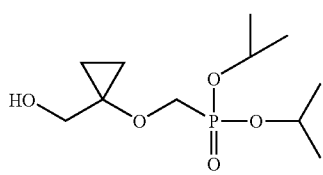
(2)

, which is a key intermediate for synthesizing an antiviral (particularly, against hepatitis B virus) nucleoside analogue of the following formula (1):

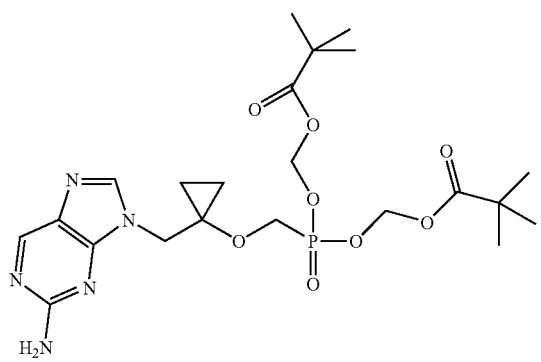
(1)

The present invention also relates to new intermediates, and a process for preparing the compound of formula (1) [compound (1), below] from the compound of formula (2) [compound (2), below] prepared according to the present invention.

BACKGROUND ART

The compound (1) is a therapeutic agent against hepatitis B (Korean Patent Application No. 2002-0003051, WO 02/057288), and the compound (2) can be used as an important reactant together with a compound of the following formula (3):

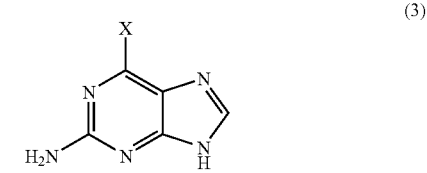
(3)

in which X represents fluorine, chlorine, bromine, or iodine, for preparing the compound (1).

Such purine derivatives as the compound (1) are known to have anticancer and antiviral activities, and ten (10) or more kinds of such derivatives including AZT, 3TC, ACV, etc. are already commercially available.

The compound (2) used as an important intermediate for preparing the compound (1) has been prepared according to the process depicted in the following Reaction Scheme 1:

Reaction Scheme 1

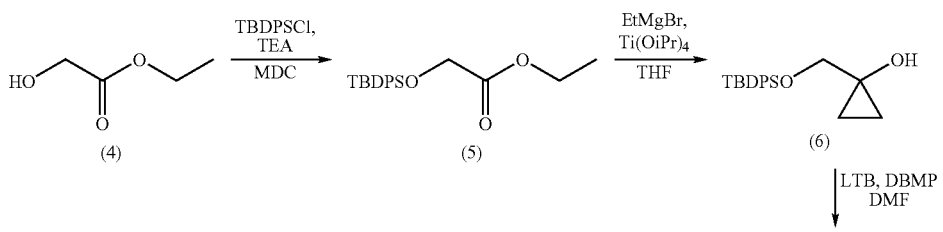

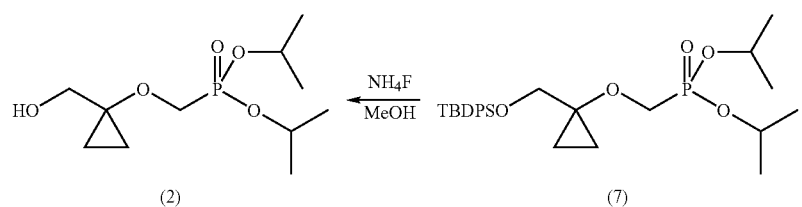

The above process of Scheme 1 uses ethyl glycolate of the following formula (4):

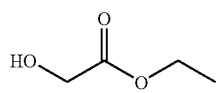
(4)

as a starting material.

In the process of Scheme 1, ethyl glycolate of formula (4) is combined with t-butyl(diphenyl)silyl chloride to give the compound of formula (5), which is reacted with ethyl magnesium bromide and titanium tetraisopropoxide according to the process (*Syn. Lett*, 07, 1053-1054, 1999) known in the art to give the cyclopropyl alcohol compound of formula (6), which is then obtained as a solid from heptane. Thus obtained compound of formula (6) is dissolved in dimethylformamide and reacted with lithium t-butoxide and diisopropylbromomethyl phosphonate to give the compound of formula (7). This compound of formula (7) is refluxed with ammonium fluoride in methanol to give the compound (2).

The above process, however, has the demerit of giving an impure form of compound (2) because diisopropylbromomethyl phosphonate used in the step of synthesizing the compound of formula (7) is remained in the reaction solution, and so always included in the finally obtained compound (2) in an amount of 7~15%. Further, poor stability of the compound of formula (6) against lithium t-butoxide during the step of synthesizing the compound of formula (7) are responsible for varied yield and difficult handling.

Therefore, it has been desired for those skilled in the art to raise purity of the compound (2) and to improve stability of the compound of formula (6) during synthesis of the compound of formula (7).

DISCLOSURE OF THE INVENTION

The present inventors thus extensively studied to improve the process for preparing the compound (2), and as a result found that the problems of the earlier process as mentioned above can be overcome by use of trityl chloride instead of t-butyl(diphenyl)silyl chloride as a reactant to give the compound (2) in high purity. The inventors also found that the compound (1) can be obtained in high yield by use of highly pure compound (2) thus obtained, and then completed the present invention.

Therefore, an object of the present invention is to provide a new process for preparing the compound (2).

It is another object of the present invention to provide new intermediates obtained during the process of preparing the compound (2).

It is a further object of the present invention to provide a process for preparing the nucleoside analogue of formula (1) useful as an antiviral agent using the compound (2) obtained by the process according to the present invention.

The present invention provides a process for preparing the compound (2) comprising the steps of reacting the compound of formula (4) with trityl chloride to prepare trityloxy-acetic acid ethyl ester of the following formula (8):

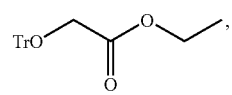
(8)

reacting the compound of formula (8) with ethyl magnesium halide to prepare 1-trityloxymethyl-cyclopropanol of the following formula (9):

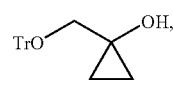
(9)

combining the 1-trityloxymethyl-cyclopropanol of formula (9) with diisopropylbromo-methylphosphonate in a solvent in the presence of a base to prepare (1-trityloxymethyl-cyclopropoxymethyl)-phosphonic acid diisopropyl ester of the following formula (10):

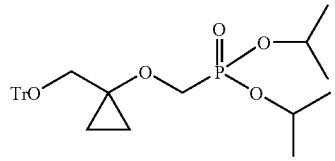
(10)

as a solid form, and converting the trityl group of the compound of formula (10) into hydroxyl group.

When carrying out the process of the present invention, N-methylpyrrolidone (NMP) can be more preferably selected as a solvent for the combination step of the cyclopropyloxy group of formula (9) with the phosphonate group to give the compound (2) in better yield and purity.

The process of the present invention can be depicted as the following Reaction Scheme 2.

Reaction Scheme 2:

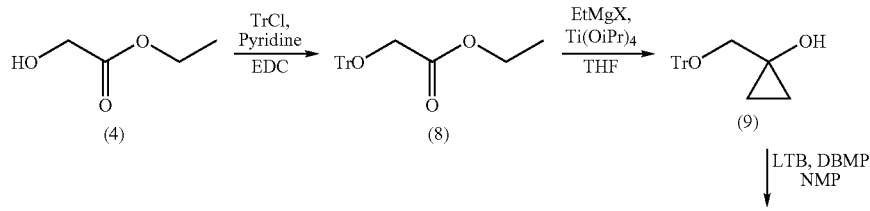

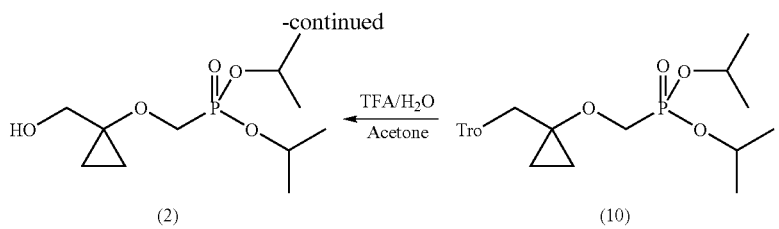

(2)                                               (10)

in which X represents fluorine, chlorine, bromine, or iodine.

The preferable amount of each reactant and reaction conditions including reaction temperature and purification process may be specifically explained below.

First, the abbreviations used in the present specification are defined as follows:

Tr: Trityl
Et: Ethyl
EDC: 1,2-Dichloroethane
THF: Tetrahydrofuran
EA: Ethyl acetate
iPr: Isopropyl
LTB: Lithium t-butoxide
NMP: N-methyl pyrrolidone
DBMP: Diisopropylbromomethyl phosphonate
MTBE: Methyl t-butyl ether
TFA: Trifluoroacetic acid
MDC: Methylene chloride
AN: Acetonitrile
Min: Minute In the first reaction step of ethyl glycolate of formula (4) with trityl chloride, 1.0 equiv. of trityl chloride (TrCl) and 1~1.3 equiv. of pyridine are added to 1.0~1.5 equiv. of the compound of formula (4), and the mixture is stirred in the presence of EDC at about 30~60° C. After the stirring, an acid-base treatment to the mixture gives the compound of formula (8), which is then treated with hexane to be converted into a solid form, or used in the next reaction without further purification. To the compound of formula (8) are introduced 2.1~3.1 equiv. of ethyl magnesium halide, preferably, ethyl magnesium chloride or ethyl magnesium bromide, and 0.2~0.6 equiv. of titanium tetraisopropoxide, and Kulinkovich reaction (*J. Am. Chem. Soc.*, 1995, 117, 9919~9920) is performed at 5~15° C. Then, aqueous citric acid solution is added thereto, and the reaction mixture is stirred and extracted to give the compound of formula (9). The compound of formula (9) is dissolved in a solvent, particularly preferably in NMP, 1.3~1.7 equiv. of DBMP and 1.5~2.0 equiv. of LTB are added thereto, and the mixture is stirred over 6 to 19 hours under the condition of not exceeding 45° C. and subjected to an acid-base treatment to give the compound of formula (10). The compound of formula (10) thus obtained is converted into a solid form by treatment with heptane under a low temperature. To the compound of formula (10) are added 1.5~2.5 equiv. of TFA and 0.1~0.5 ml/g of H$_2$O, and the mixture is stirred at room temperature. After the stirring, an acid-base treatment, filtration of thus produced solid, and extraction give the compound (2). Here, preferably, the acid-base treatment is carried out with sodium hydroxide, and the extraction with methylene chloride.

The process of the present invention produces the compound (2) in high purity running into 98 to 100%.

Also, the compounds of formulae (9) and (10) obtained as intermediates for the process of the present invention are themselves novel compounds. Therefore, the present invention further provides these novel intermediate compounds.

The compound (2) prepared by the above process is a key intermediate for synthesizing the nucleoside analogue of formula (1) as mentioned above. Specifically, the compound (1) can be prepared by a process comprising the steps of introducing a leaving group into the compound (2) to prepare a compound of the following formula (11):

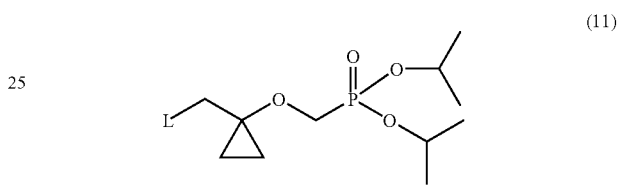

(11)

in which L represents a leaving group, preferably, methanesulfonyloxy, para-toluenesulfonyloxy, or halogen, coupling the compound of formula (11) with the compound of formula (3) to prepare a compound of the following formula (12):

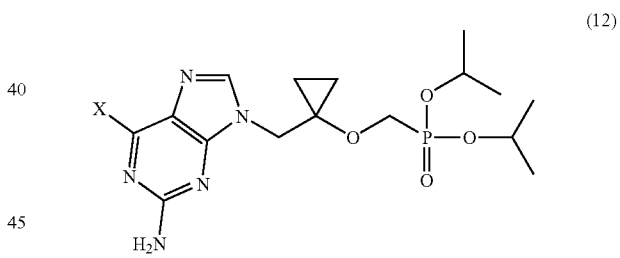

(12)

in which X is defined as above, hydrolyzing the compound of formula (12) to prepare a compound of the following formula (13):

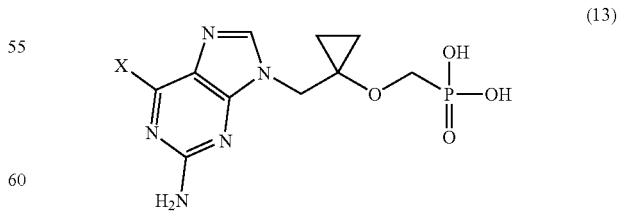

(13)

in which X is defined as above, removing the group X from the compound of formula (13) and concurrently introducing t-butylcarbonyloxymethyl group into the phosphonic acid moiety.

The detailed reaction conditions of the above process are described in the applicant's prior application (Korean Patent Application No. 2002-0003051, WO 02/057288). Therefore, the present invention provides a process for preparing the compound (1) from the compound (2) prepared by a process depicted in Reaction Scheme 2.

The present invention will be more specifically explained by the following examples. However, it should be understood that these examples are intended to illustrate the present invention but not in any manner to limit the scope of the present invention.

In the examples below, the HPLC conditions for determining the completion of reaction are as follows:

[HPLC conditions]
Column: Capcell pak $C_{18}$ (Type: MG 5 μm; Size: 4.6 mm I.D×250 mm)
Wavelength (λ): 254 nm
Flow rate: 1.0 ml/min
Gradient condition: Start: 20/80 ($H_2O$/AN, 0.1% TFA), 5 min: 20/80, 7 min: 0/100, 10 min: 0/100, 12 min: 20/80

EXAMPLES

Example 1

Preparation of trityloxy-acetic Acid Ethyl Ester (8)

Trityl chloride (279 g, 1.0 mol) was dissolved in EDC (680 ml, 5 ml/g with respect to ethyl glycolate), and ethyl glycolate (135 g, 1.3 mol) was added to the mixture. Pyridine (99 g, 1.25 mol) was added thereto, and the mixture was stirred for 19 hours at 40° C. After completion of the reaction was confirmed by HPLC, 0.5 N aqueous hydrochloric acid solution (270 ml, 2 ml/g with respect to ethyl glycolate) was added to make the reaction solution a two-phase solution, which was then extracted. After the extraction was performed once again, EDC was distilled under reduced pressure. In order to obtain the compound of formula (8) as a solid form, hexane (680 ml) was added to the concentrated compound, the temperature was lowered to 0° C., and the mixture was stirred for about 3 hours and filtered.

| | [HPLC] Compound: | |
|---|---|---|
| | TrCl | Compound (8) |
| RT: | 5.38 | 8.58 |
| Area %: | 2.39 | 83.93 |

$^1$H NMR (400 MHz, $CDCl_3$) δ 1.23 (t, 3H, J=8 Hz), 3.78 (s, 2H), 4.14 (q, 2H, J 8 Hz), 7.26~7.22 (m, 3H), 7.33~7.29 (m, 6H), 7.50~7.47 (m, 6H)
$^{13}$C NMR (400 MHz, $CDCl_3$) δ 10.8, 57.3, 59.3, 84.0, 123.9, 124.6, 125.3, 140.0, 166.7

Example 2

Preparation of 1-trityloxymethyl-cyclopropanol (9)

Tetrahydrofuran [1040 ml, 3 ml/g with respect to the compound of formula (8)] was added to the compound of formula (8) prepared in Example 1 on the premise that the yield of Example 1 is 100%, and the mixture was cooled to 0° C. Titanium tetraisopropoxide (113.8 g, 0.4 mol) was added thereto, and ethyl magnesium bromide (1500 ml, 3.0 mol, 1 M concentration) was added thereto dropwise at 5~15° C. over 3~6 hours. After completion of the reaction was confirmed by HPLC, 20% aqueous citric acid solution [1790 ml, 5 ml/g with respect to the compound of formula (8)] was added to the reaction solution under the condition of not exceeding 35° C., which was stirred for about 1 hour. After the stirring, tetrahydrofuran therein was distilled under reduced pressure, and the residue was extracted twice, first with 1390 ml [4 ml/g with respect to the compound of formula (8)] of ethyl acetate and second with 690 ml [2 ml/g with respect to the compound of formula (8)] of the same. Thus resulted organic layer was washed with saturated aqueous $NaHCO_3$ solution [690 ml, 2 ml/g with respect to the compound of formula (8)], and concentrated under reduced pressure to give the title compound of formula (9).

| | [HPLC] Compound: | |
|---|---|---|
| | TrOH | Compound (9) |
| RT: | 5.40 | 6.23 |
| Area %: | 5.07 | 78.54 |

$^1$H NMR (400 MHz, $CDCl_3$) δ 0.45 (dd, 2H, J=8 Hz), 0.80 (dd, 2H, J=8 Hz), 2.59 (s, 1H), 3.18 (s, 2H), 7.23~7.32 (m, 9H), 7.45~7.47 (m, 6H)
$^{13}$C NMR (400 MHz, $CDCl_3$) δ 8.4, 51.9, 63.9, 83.0, 123.7, 124.6, 125.3, 140.5

Example 3

Preparation of (1-trityloxymethyl-cyclopropoxymethyl)-phosphonic Acid Diisopropyl Ester (10)

To the compound of formula (9) (261.25 g, 0.79 mol) obtained by concentration under reduced pressure in Example 2 (it was assumed that the compound of formula (9) was obtained in a yield of 79% starting from Example 1, since the peak area by HPLC was 78.54%) were added NMP [1050 ml, 4 ml/g with respect to the compound of formula (9)] and DBMP (307 g, 1.2 mol). To the reaction mixture was added LTB (107 g, 1.3 mol), which was then stirred under the condition of not exceeding 45° C. After about 6~19 hours, completion of the reaction was confirmed by HPLC, and 14% aqueous $NH_4Cl$ solution [1830 ml, 7 ml/g with respect to the compound of formula (9)] was added thereto to stop the reaction. MTBE [first: 1050 ml, 4 ml/g with respect to the compound of formula (9); second: 520 ml, 2 ml/g with respect to the compound of formula (9)] was added thereto twice for phase-separation. Thus obtained organic layers were combined and washed with 21% aqueous NaCl solution [1650 ml, 6.3 ml/g with respect to the compound of formula (9)]. The remaining organic layer was concentrated under reduced pressure, and heptane [1300 ml, 5 ml/g with respect to the compound of formula (8)] was added thereto. The mixture was cooled to −10° C., and filtered after about 3 hours to give the title compound of formula (10) (586 g, Purity 96.23%, Yield 71.3%) as a solid.

| | [HPLC] Compound: | | |
|---|---|---|---|
| | TrOH | Compound (9) | Compound (10) |
| RT: | 5.24 | 6.02 | 9.26 |
| Area %: | 0.10 | 0.09 | 96.23 |

[NMR] No other peaks were observed besides the peak for the compound of formula (10).
$^1$H NMR (400 MHz, $CDCl_3$) δ 0.54 (dd, 2H, J=8 Hz), 0.80 (dd, 2H, J=8 Hz), 1.33~1.29 (m, 12H), 3.22 (s, 2H), 3.92 (d, 2H, J=8 Hz), 4.67~4.76 (m, 2H), 7.21~7.31 (m, 9H), 7.43~7.46 (m, 6H)

$^{13}$C NMR (400 MHz, CDCl$_3$) δ 11.9, 24.4, 24.4, 24.5, 24.6, 63.5, 63.8, 64.0, 65.1, 67.3, 71.3, 71.4, 86.9, 127.4, 128.3, 129.1, 144.3

Example 4

Preparation of diisopropyl {[1-(hydroxymethyl)-cyclopropyl]oxy}methylphosphonate (2)

The compound of formula (10) obtained in Example 3 (59.15 g, 116.3 mmol) was dissolved in acetone [59.2 ml, 1 ml/g with respect to the compound of formula (10)], H$_2$O (5.9 ml, 327.8 mmol) and TFA (26.52 g, 232.6 mmol) were added, and the mixture was stirred at room temperature. After the portion of the compound of formula (10) was confirmed 7% or less by HPLC, 3N aqueous NaOH solution [75 ml, 2.6 ml/g with respect to the compound of formula (10)] was added thereto, and acetone was removed therefrom by distillation under reduced pressure. The solid produced during the reaction was filtered off, and the filtrate was extracted twice with methylene chloride [118.3 ml×2, 2 ml/g with respect to the compound of formula (10)]. Thus obtained organic layer was concentrated under reduced pressure to give the title compound (2) [31.71 g, Purity 98%, Yield with respect to the compound of formula (10) 102.4%].

| | [HPLC] Compound: | |
|---|---|---|
| | TrOH | Compound (10) |
| RT: | 5.14 | 9.20 |
| Area %: | 93.58 | 5.07 |

[NMR] Only the peak for methylene chloride, the solvent, besides the peak for the compound (2) was observed.

$^1$H NMR (400 MHz, DMSO) δ 0.55 (dd, 2H, J=8 Hz), 0.72 (dd, 2H, J=8 Hz), 1.22~1.24 (m, 12H), 3.32 (s, 2H), 3.53 (d, 2H, J=4 Hz), 3.81 (d, 2H, J=8 Hz), 4.53~4.72 (m, 2H), 4.73 (t, 1H)

$^{13}$C NMR (400 MHz, DMSO) δ 7.44, 20.7, 20.75, 20.85, 20.88, 58.81, 60.47, 60.69, 61.62, 61.77, 67.12, 67.18

As explained above, when trityl chloride is used according to the present invention, the intermediate compound of formula (10) can be obtained as a solid, which solves the problem of the prior art that diisopropylbromomethyl phosphonate is not removed but retained in the compound (2) to lower the purity thereof. Particularly, if N-methylpyrrolidone is selected instead of dimethylformamide as a solvent for preparing the compound of formula (10), stability of the compound of formula (9) against lithium t-butoxide is highly improved to affect the purity and yield of the compound (2) in a favorable manner. Also, the compound (1) useful as an antiviral agent can be advantageously prepared with high yield by using the highly pure compound (2) obtained according to the present invention.

The invention claimed is:

1. A process for preparing a compound of the following formula (2):

(2)

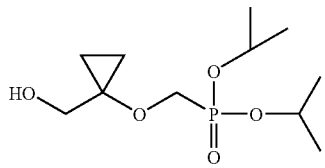

comprising the steps of reacting a compound of the following formula (4):

(4)

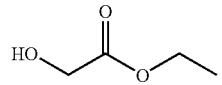

with trityl chloride to prepare trityloxy-acetic acid ethyl ester of the following formula (8):

(8)

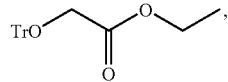

reacting the compound of formula (8) with ethyl magnesium halide to prepare 1-trityloxymethyl-cyclopropanol of the following formula (9):

(9)

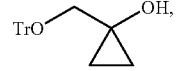

combining the 1-trityloxymethyl-cyclopropanol of formula (9) with diisopropylbromo-methylphosphonate in a solvent in the presence of a base to prepare (1-trityloxymethyl-cyclopropoxymethyl)-phosphonic acid diisopropyl ester of the following formula (10):

(10)

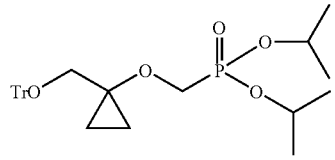

as a solid form, and converting the trityl group of the compound of formula (10) into a hydroxyl group.

2. The process of claim 1, wherein the solvent used in the step of reacting the compound of formula (9) to prepare the compound of formula (10) is N-methylpyrrolidone.

3. The process of claim 1 or 2, wherein the base used in the step of reacting the compound of formula (9) to prepare the compound of formula (10) is lithium t-butoxide.

4. The process of claim 1 or 2, wherein ethyl magnesium halide is ethyl magnesium chloride or ethyl magnesium bromide.

5. The process of claim 1 or 2, wherein ethyl magnesium halide is reacted with the compound of formula (8) in the presence of titanium tetraisopropoxide.

6. The process of claim 1 or 2, wherein the product obtained after the conversion of the trityl group into the hydroxyl group in the compound of formula (10) is treated with sodium hydroxide, the resulting solid is filtered off, and the filtrate is extracted with methylene chloride to give the compound of formula (2).

7. A compound of the following formula (10):

(10)

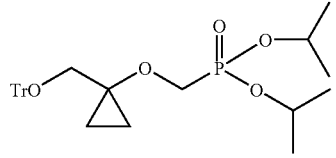

8. The process of claim 1, wherein the compound of formula (2) is obtained in a purity of 98 to 100%.

* * * * *